United States Patent
Somoto et al.

(10) Patent No.: US 8,921,310 B2
(45) Date of Patent: Dec. 30, 2014

(54) METHOD FOR ACCELERATING MAMMALIAN BODY FAT METABOLISM

(75) Inventors: Yuuki Somoto, Yokohama (JP); Masayuki Ikeda, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 831 days.

(21) Appl. No.: 12/281,485

(22) PCT Filed: Jun. 5, 2007

(86) PCT No.: PCT/JP2007/061361
§ 371 (c)(1),
(2), (4) Date: Sep. 3, 2008

(87) PCT Pub. No.: WO2007/142230
PCT Pub. Date: Dec. 13, 2007

(65) Prior Publication Data
US 2009/0012001 A1 Jan. 8, 2009

(30) Foreign Application Priority Data
Jun. 9, 2006 (JP) ................................. 2006-161076

(51) Int. Cl.
| A61K 38/00 | (2006.01) |
| A61K 38/16 | (2006.01) |
| A61K 38/17 | (2006.01) |
| A23K 1/16  | (2006.01) |
| A23L 1/305 | (2006.01) |
| A61K 35/20 | (2006.01) |

(52) U.S. Cl.
CPC .............. *A61K 38/17* (2013.01); *A23K 1/1631* (2013.01); *A23L 1/3056* (2013.01); *A61K 35/20* (2013.01); *A23V 2002/00* (2013.01)
USPC .......... 514/4.8; 514/5.7; 514/21.2; 514/21.92

(58) Field of Classification Search
CPC ... A61K 38/00; A61K 38/17; A61K 38/1709; A61K 35/20; A61K 38/018; A23L 1/305; A23L 1/3053; A23L 1/3056; A23J 1/202; A23J 3/10; A23J 3/08; A23J 1/20; A23V 2250/54246; A23V 2200/328; C07K 14/47; C07K 14/4732; A23C 21/00; A23C 21/06; A23C 9/1307; A23C 9/1512
See application file for complete search history.

(56) References Cited

U.S. PATENT DOCUMENTS

| 6,207,638 | B1 | 3/2001 | Portman |
| 7,666,996 | B2 * | 2/2010 | Sidelman .................. 530/360 |
| 2003/0165574 | A1 | 9/2003 | Ward et al. |
| 2004/0234666 | A1 * | 11/2004 | Law et al. ................. 426/580 |
| 2005/0148504 | A1 | 7/2005 | Katunuma et al. |
| 2006/0280802 | A1 | 12/2006 | Campbell et al. |

FOREIGN PATENT DOCUMENTS

| DE | 19510765 A1 | 9/1996 |
| JP | 05-146258 | 6/1993 |
| JP | 06-040936 | 2/1994 |
| JP | 06-211690 | 8/1994 |
| JP | 2000-287656 | 10/2000 |
| JP | 2003-523368 | 8/2003 |
| JP | 2006-507217 | 3/2006 |
| JP | 2006-501299 | 12/2006 |
| WO | 03018606 A2 | 3/2003 |
| WO | 2004/050118 A1 | 6/2004 |

OTHER PUBLICATIONS

Ginger et al 1999. Comp. Biochem and Phys Part B 124:133-145.*
Prewitt et al. 1991. Am. J. Clin. Nutr. 54:304-10.*
Wing et al. 2001. Obesity Research 9:271S-275S.*
Parker et al. 2002. Diabetes Care 25:425-430.*
Zamboni et al. 1993. Am J. Clin Nutr. 58:29-34.*
Morabia et al 2005. Am J. of Pub Health. 95:632-635.*
Lynch et al. 2001. J. Appl Physiol. 90:99-104.*
Scharrer et al. 1970. Am. J. of Physiol. 218:400-404.*
Izumi Kawasaki et al.; Japanese Society of Nutrition and Food Science, Abstract Writings, 3H-6a, 2006, p. 343.
Yi-Chin Lin et al.; Dairy Calcium is Related to Changes in Body Composition during a Two-Year Exercise Intervention in Young Women, Journal of the American College of Nutrition, vol. 19, No. 6, 2000, pp. 754-760.
Michael B. Zemel et al.; Regulation of adiposity by dietary calcium, FASEB Journal, vol. 14, 2000, pp. 1132-1138.
Philippe Cayot et al.; Purification of α s-, β- and κ-caseins by batchwise ion-exchange separation, Journal of Dairy Research, vol. 59, 1992, pp. 551-556.
Lorraine Ghibaudi et al.; Fat Intake Affects Adiposity, Comorbidity Factors, and Energy Metabolism of Sprague-Dawley Rats, Obesity Research, vol. 10, No. 9, 2002, pp. 956-963.
European Search Report issued in Euopean Patent Application No. 07744713.4, dated May 30, 2012, 6 pages.
Chinese Official Action issued in Chinese Patent Application No. 200780010697.9, mailed Jan. 4, 2012, 8 pages.
Ho, C. et al., The Polymerization of Bovine as-Casein B*, The Journal of Biological Chemistry, Feb. 10, 1967, pp. 551-553, vol. 242, No. 3.

* cited by examiner

*Primary Examiner* — Shulamith H Shafer
(74) *Attorney, Agent, or Firm* — Wood, Herron & Evans, LLP

(57) ABSTRACT

The present invention relates to an agent for improving lipid metabolism, a food/drink, and a feed, containing αs-casein as an active ingredient thereof. In addition, the present invention relates to an agent for suppressing body weight gain, an agent for reducing body fat, and an agent for reducing blood lipid, containing the agent for improving lipid metabolism.

16 Claims, 4 Drawing Sheets

METHOD FOR ACCELERATING MAMMALIAN BODY FAT METABOLISM

TECHNICAL FIELD

The present invention relates to a medicine, a food or drink, or a feed, which contains αs-casein, which is one of caseins derived from milk, as an active ingredient and which can improve lipid metabolism. In more detail, the present invention relates to a medicine, a food or drink, or a feed, which can normalize the body fat ratio by accelerating or improving metabolism of fat, particularly subcutaneous fat and visceral fat, excessively ingested via a food/drink or feed and accumulated in the living body. The present invention also relates to a medicine, a food or drink, or a feed, which can normalize the levels of the lipids in the blood, such as cholesterol or neutral lipids in the blood.

BACKGROUND ART

It is known that obesity tends to cause many risk factors such as lipid metabolism abnormality, hypertension, glucose tolerance disorder, or the like. Total cholesterol and neutral lipids are increased, while the HDL (high-density lipoprotein) is decreased, in accordance with an increase in the accumulation of visceral fat. In addition, the qualitative abnormality of the LDL (low-density lipoprotein) is caused and the lipid metabolism is quantitatively and qualitatively influenced by visceral fat accumulation. Lipid metabolism abnormalities often occur in obese persons, and total cholesterol and neutral lipid content in the blood are particularly increased.

In recent years, lifestyle-related diseases such as diabetes have been increasing, and countermeasures for inhibiting such diseases have been reported. Obesity is considered to be a major cause of hyperlipidemia, hypertension, diabetes, and other lifestyle-related diseases. It is supposed that obesity should be prevented or the level of obesity should be decreased so as to prevent such diseases. In addition, obesity tends to be considered unfavorable in terms of personal appearance and beauty. Because of this, anorexia nervosa or hyperphagia is occasionally caused, and thereby medical treatment is required.

Thus, awareness of obesity is growing, and the Japan Society for the Study of Obesity defined in 2000 the "obesity symptom" associated with health disorders as a novel type of obesity and shows criteria for diagnosis of the obesity symptom. That is, the "obesity symptom" which causes disorders and therefore requires treatments has been distinguished from "obesity" in which body fat is accumulated, and the diagnosis thereof has been established. In addition, the criteria for diagnosis of "metabolic syndrome" which often causes lifestyle-related diseases was compiled in April, 2005. In the criteria, accumulation of visceral fat is required to be checked by measuring the waist perimeter. In addition, exercise therapy, diet modifications, and the like have been proposed in order to prevent obesity or reduce the level of obesity.

Milk tends not to be considered as a suitable food for reducing body-weight, since milk contains a fatty ingredient. In fact, milk is primarily a food for growing children, and contains lipids as an energy source. The lipids in milk are utilized for making butter and excessive intake of butter is considered to cause the obesity, and thereby milk tends also to be considered a fattening food.

However, babies drinking milk do not gain excessive weight, and it has not been reported that babies suffer from obesity which results in lifestyle-related diseases. That is, it has been suggested that milk contains a substance which enables effective utilization of lipids originally contained in milk as an energy source.

For example, Kawasaki et al., compared a milk-intake group which ingested 200 ml of milk per day to reduce body weight for four months while receiving dietary instruction and exercising with a control group which was not required to ingest milk, as shown in Non-Patent Document 1 described below. As a result, although there was almost no difference between the milk-intake group and the control group in terms of decreasing rate of body weight between before and after reducing the body weight for four-months, the ratio of the central adiposity in the milk-intake group was distinctly decreased in comparison with that of the control group. It has been reported that such an effect was considered to be exhibited by calcium or vitamin D contained in milk.

In addition, it has also been reported in the following Non-Patent Documents 2 and 3 that calcium in milk or a milk product has activities for reducing body weight.

In addition, the following Patent Document 1 discloses a food or drink for suppressing the blood lipid level containing a peptide obtained from hydrolyzing casein derived from milk with trypsin as an active ingredient thereof, relating to effects of a protein in milk or a hydrolysate or peptide thereof, for example. The following Patent Document 2 discloses the use of β-casein A2 for reducing cholesterol level, lipid level, triglyceride level, or the like, and a nutritional supplement containing β-casein A2. In addition, the following Patent Document 3 discloses a nutrition composition containing a milk mineral mixture and protein components such as κ-casein fragments 106-169, for effectively enhancing a decrease of body weight and/or suppressing an increase in body weight.

Patent Document 1 Japanese Unexamined Patent Application, First Publication No. H6-211690.
Patent Document 2 Published Japanese translation of No. 2006-501299 of PCT International Publication.
Patent Document 3 Published Japanese translation of No. 2006-507217 of PCT International Publication.
Non-Patent Document 1 Journal of Japanese Society of Nutrition and Food Science, Proceedings of the annual meeting 2006, Page 343.
Non-Patent Document 2 Journal of the American College of Nutrition, Vol. 19, 2000, Pages 754 to 760.
Non-Patent Document 3 FASEB Journal, Vol. 14, 2000, Pages 1132 to 1138.

DISCLOSURE OF THE INVENTION

Problems to be Solved by the Invention

However, the prior art as described above does not always exhibit sufficient effects, and the development of a medicine, food/drink, or feed, which has a high degree of safety, exhibits excellent activities for improving lipid metabolism, and is effective against lifestyle-related diseases caused by the obesity, has been required.

The present invention has been accomplished in view of the above-mentioned circumstances, and has as an object thereof to provide a medicine which has a high degree of safety, exhibits excellent activities for improving lipid metabolism, and is effective against lifestyle-related diseases caused by the obesity.

Means for Solving the Problems

The inventors of the present invention have investigated an active ingredient which is cheap and safe and can improve lipid metabolism in the living body. In more detail, the inventors focused on a milk component which is a naturally-derived component eaten over a long time, and researched substances which can exhibit unprecedented excellent activities for improving lipid metabolism. As a result, the inventors found that αs-casein exhibits significant activities for improving lipid metabolism in comparison with other casein fractions, such as β-casein or κ-casein, and completed the present invention.

Activities of α-casein, particularly lipid-metabolism-improving activities of αs-casein, were not heretofore known at all.

The present invention relates to an agent for improving lipid metabolism containing αs-casein as an active ingredient thereof.

In addition, the present invention relates to an agent for suppressing body weight gain, an agent for reducing body fat, and an agent for reducing blood lipid, containing the agent for improving lipid metabolism.

In addition, the present invention relates to use of αs-casein for the manufacture of the agent for improving lipid metabolism, the agent for suppressing body weight gain, the agent for reducing body fat, and the agent for reducing blood lipid.

In addition, the present invention relates to a method for improving mammalian lipid metabolism, including: administering the agent for improving lipid metabolism.

In addition, the present invention relates to a method for suppressing mammalian body weight gain, including administering the agent for suppressing body weight gain.

In addition, the present invention relates to a method for reducing mammalian body fat, including administering the agent for reducing body fat.

In addition, the present invention relates to a method for reducing mammalian blood lipid level, including administering the agent for reducing blood lipid.

In addition, the present invention relates to a food or drink for improving lipid metabolism, containing αs-casein as an active ingredient thereof, and use of αs-casein for the manufacture of the food or drink.

The food or drink may be in the form of a health food, a functional food, a food for a specified use, a food with a nutrient function claim, or a food for a specified health use.

In addition, the present invention relates to a feed for improving lipid metabolism, containing αs-casein as an active ingredient thereof.

The present invention relates to a method of using αs-casein as a medicine to improve lipid metabolism, suppress body weight gain, reduce body fat, or reduce blood lipid level.

Effects of the Invention

In accordance with the present invention, the agent for improving lipid metabolism which has a high degree of safety and exhibits excellent activities for improving lipid metabolism.

The effects exhibited by the agent for improving lipid metabolism according to the present invention are as follows.
(1) The agent for improving lipid metabolism according to the present invention has an activity for accelerating the metabolism of subcutaneous fat and visceral fat excessively accumulated in a living body due to excessive food ingestion. Such activity exhibits significant effects on the suppression of body weight gain, and the reduction of body fat such as visceral fat. Accordingly, the agent for improving lipid metabolism is useful for preventing obesity or decreasing the level of obesity.
(2) The agent for improving lipid metabolism according to the present invention has an activity for reducing blood lipids such as cholesterol or neutral lipids in blood, the blood lipids causing cardiovascular diseases when retained in blood vessels due to excessive food intake. Accordingly, the agent for improving lipid metabolism is useful for preventing or curing diseases such as myocardial infarction, or cerebral infarction.
(3) The agent for improving lipid metabolism according to the present invention has a high degree of safety with regard to human and animals, and can be routinely ingested over a long period of time without worrying about side-effects. Accordingly, the agent for improving lipid metabolism is suitable for preventing and/or treating lifestyle-related diseases such as hyperlipidemia, hypertension, or diabetes, which are considered to be caused by obesity.
(4) The agent for improving lipid metabolism can be provided at a low cost, since αs-casein formulated as an active ingredient thereof can be stably produced on a large scale from a raw material available at a relative low cost as a biomaterial, such as milk. In addition, the agent for improving lipid metabolism may be provided in the form of a food/drink or feed. Thus, the agent for improving lipid metabolism which can be routinely ingested over a long period of time from the standpoint of cost, and a food/drink or feed containing the agent for improving lipid metabolism can be provided.

Accordingly, an agent for suppressing body weight gain with a high degree of safety can be provided according to the present invention.

In addition, an agent for reducing body fat with a high degree of safety can be provided according to the present invention.

In addition, an agent for reducing blood lipid with a high degree of safety can be provided according to the present invention.

BEST MODE FOR CARRYING OUT THE INVENTION

Figure 1:
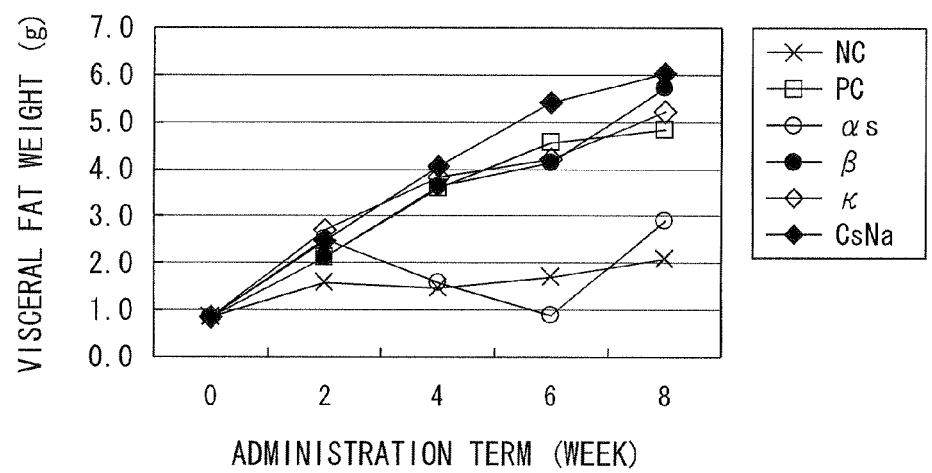
FIG. 1 is a graph showing the variation of visceral fat weight in a test over the administration period.

The preferable aspects of the present invention will be circumstantially explained. The present invention is not limited to the following preferable aspects, and can be unrestrictedly modified in the scope of the present invention. In the present specification, a percentage indicates percentage by mass unless otherwise so indicated.

The activities for improving lipid metabolism according to the present invention accelerates metabolism of subcutaneous fat and visceral fat accumulated in the living body mainly due to excessive food ingestion (hereinafter, abbreviated to "body fat"), and normalizes the body fat ratio obtained by dividing the total weight of the adipose tissues in the body by the body weight. Such activities specifically achieve suppressing body weight gain, reducing body fat, and/or reducing blood lipid level.

The agent for improving lipid metabolism according to the present invention can be favorably used as an agent for suppressing body weight gain, an agent for reducing body fat, and/or an agent for reducing blood lipid. In addition, an agent for suppressing body weight gain containing the agent for improving lipid metabolism, an agent for reducing body fat containing the agent for improving lipid metabolism, and an agent for reducing blood lipid containing the agent for improving lipid metabolism are provided. In addition, a method for improving mammalian lipid metabolism by administering the agent, a method for suppressing body weight gain by administering the agent, a method for reducing body fat by administering the agent, and a method for reducing blood lipid levels by administering the agent are provided.

Examples of a "mammal" include humans and livestock animals (such as, for example, horses, dogs, cats, rabbits, cows, sheep, and goats).

The activities according to the present invention metabolize lipids excessively accumulated in the body without substantially decreasing essential lipids, as shown in the following tests. In addition, almost no influence on tissues excluding adipose tissues (lean body mass) are recognized.

According to the present invention, the treatment causes remission (improvement) of symptoms or cures disorders. The treatment effects achieved by the present invention are preferably to induce remission and keep the condition thereof. According to the present invention, the activities for improving lipid metabolism are achieved by routinely administering or ingesting $\alpha$s-casein as an active ingredient without causing any side-effects.

$\alpha$s-casein used in the present invention can be industrially manufactured using a raw material such as milk in accordance with a conventional method such as an ion chromatography method. For example, $\alpha$s-casein can be manufactured in accordance with a method disclosed in Journal of Dairy Research (J. Dairy Research), Vol. 59, 1992, Pages 551 to 556.

Alternatively, a commercially available $\alpha$s-casein derived from natural sources (manufactured by SIGMA, for example), a recombinant $\alpha$s-casein, or the like, may be used, if desired.

It is preferable that $\alpha$s-casein be derived from mammalian milk. It is more preferable that $\alpha$s-casein be derived from the milk of a cow, a sheep, or a goat, if the administration target is human. The reason for this is that such milk has been consumed by humans over a long period of time, and therefore safety for human beings is ensured to an extremely high level. Among them, $\alpha$s-casein derived from cow milk is preferably used.

The administration route of the agent for improving lipid metabolism, the agent for suppressing body weight gain, the agent for reducing body fat, or the agent for reducing blood lipid, according to the present invention is not particularly limited. For example, an oral route or a parenteral route such as an enteral route may be adopted.

$\alpha$s-casein contained as an active ingredient in the agent for improving lipid metabolism according to the present invention is contained in foods such as milk, and routinely ingested without exhibiting toxic consequences. Even if $\alpha$s-casein is ingested for a long term, almost no side-effects are recognized. That is, safety of $\alpha$s-casein is very high when ingested, and $\alpha$s-casein is suitable for oral administration or enteral administration.

The agent for improving lipid metabolism according to the present invention may consist of $\alpha$s-casein, or may further comprise other components. In the both cases, it is preferable that the agent for improving lipid metabolism be formulated in a form suitable for the intended purpose thereof.

The agent for suppressing body weight gain, the agent for reducing body fat, and the agent for reducing blood lipid, according to the present invention, may consist of the agent for improving lipid metabolism, or may further comprise other components.

The form of the agent for improving lipid metabolism, the agent for suppressing body weight gain, the agent for reducing body fat, or the agent for reducing blood lipid is not particularly limited. For example, the form thereof may be a well-known oral dosage form such as, for example, tablet, capsule, trochisci, syrup, granule, powder, emulsion, or spray.

Alternatively, the form may be a parenteral dosage form such as, for example, suppository, injection, ointment, or tape.

Although the dosage of $\alpha$s-casein formulated in the agent for improving lipid metabolism as an active ingredient thereof depends on the form, symptoms, age, body weight, and the like, the dosage is preferably 80 mg/kg body weight per day or more in order to effectively achieve at least one selected from the group consisting of an activity for improving lipid metabolism, an activity for suppressing body weight gain, an activity for reducing body fat, and an activity for reducing blood lipid levels. Although the upper limit of the dosage is not particularly limited since $\alpha$s-casein has a high degree of safety, the activities for improving lipid metabolism can be sufficiently achieved by administering a dosage of approximately 320 mg/kg body weight per day. It is preferable that the upper limit of the dosage be 320 mg/kg body weight per day, since almost no change can be recognized in the activities for improving lipid metabolism even if the dosage is further increased.

It is preferable that the agent for improving lipid metabolism, the agent for suppressing body weight gain, the agent for reducing body fat, and the agent for reducing blood lipid, according to the present invention, be formulated so that the daily dosage of $\alpha$s-casein falls within the above-mentioned range, and be administered so that the daily dosage of $\alpha$s-casein falls within the above-mentioned range.

$\alpha$s-casein can be formulated appropriately with an optional additive such as a pharmaceutically accepted vehicle in accordance with conventional methods, for example. An additive, such as, for example, a vehicle, binder, disintegrant, lubricant, stabilizer, taste- and smell-masking agent, diluent, or solvent for injection, may be used for formulation.

If the agent for improving lipid metabolism is a composition containing $\alpha$s-casein and other components such as additives, the content of $\alpha$s-casein in the composition is not particularly limited, however, the content is generally 0.1 to 90% by mass, preferably 0.5 to 40% by mass, and more preferably 1 to 20% by mass.

If the agent for suppressing body weight gain, the agent for reducing body fat, or the agent for reducing blood lipid is a composition containing the agent for improving lipid metabolism and other components, the content of the agent for improving lipid metabolism in the composition is not particularly limited, however, the content is generally 0.1 to 90% by mass, preferably 0.5 to 40% by mass, and more preferably 1 to 20% by mass.

Examples of the vehicle include saccharide derivatives such as lactose, saccharose, glucose, mannitol, sorbitol, and the like; starch derivatives such as corn starch, potato starch, α-starch, dextrin, and carboxymethyl starch; cellulose derivatives such as crystalline cellulose, hydroxypropyl cellulose, hydroxypropylmethyl cellulose, carboxymethyl cellulose, and carboxymethyl cellulose calcium; gum arabic; dextran; pullulan; silicate derivatives such as light anhydrous silicate, synthetic aluminium silicate, and magnesium metasilicate aluminate; phosphate derivatives such as calcium phosphate; carbonate derivatives such as calcium carbonate; sulfate derivatives such as calcium sulfate, and the like.

Examples of the binder include gelatine; polyvinylpyrrolidone; macrogol, and the like, in addition to the above-mentioned vehicle.

Examples of the disintegrant include chemically-modified starch or cellulose derivatives such as croscarmellose sodium, carboxymethyl sodium starch, and cross-linked polyvinylpyrrolidone, in addition to the above-mentioned vehicle.

Examples of the lubricant include talc; stearic acid; metal stearates such as calcium stearate, and magnesium stearate; colloidal silica; waxes such as bean gum, and spermaceti; boracic acid; glycol; carboxylic acids such as fumaric acid, and adipic acid; sodium carboxylates such as sodium benzoate; sulfates such as sodium sulfate; leucine; lauryl sulfates such as sodium lauryl sulfate, and magnesium lauryl sulfate; silicas such as silicic acid anhydride, and hydrated silicic acid; starch derivatives, and the like.

Examples of the stabilizer include p-hydroxybenzoate esters such as methylparaben, and propylparaben; alcohols such as chlorobutanol, benzyl alcohol, and phenylethyl alcohol; benzalkonium chloride; acetic anhydride; sorbic acid, and the like.

Examples of the taste- and smell-masking agent include sweeteners, acidic ingredients, fragrances, and the like.

Examples of the solvent for injection include water, ethanol, glycerin, and the like.

In addition to medicinal applications, the agent for improving lipid metabolism according to the present invention may be formulated in a food/drink or a feed for oral administration.

The food or drink containing the agent for improving lipid metabolism according to the present invention is a food or drink containing αs-casein as an active ingredient and having activities for improving lipid metabolism. The food or drink can be applied for various purposes utilizing activities for improving lipid metabolism. The food or drink is preferably applied for achieving the suppression of body weight gain, the reduction of body fat, and/or the reduction of blood lipid levels.

The food or drink can be prepared, for example, by formulating αs-casein with saccharides such as dextrin or starch; proteins such as gelatin, soy-bean protein, or corn protein; amino acids such as alanine, glutamine, or isoleucine; polysaccharides such as cellulose, or gum arabic; oils and fats such as soybean oil, or medium chain fatty acid triglyceride, appropriately.

The food or drink is preferably in a form which enables routine ingestion thereof. For example, the food or drink may be a drink such as soft drink, carbonated drink, nutritional drink, fruit drink, or lactic acid drink (including concentrated stock solution or modified powders thereof); a frozen dessert such as ice cream, ice sherbet, or shaved ice; noodles such as buckwheat noodles, Japanese wheat noodles, bean-starch vermicelli, Chinese dumpling wrap, Chinese shao mai skin, Chinese noodle, or instant noodle; a confectionery such as sweet drop, chewing gum, candy, gum, chocolate, tablet candy, snack food, biscuit, jelly, jam, cream, or baked confectionery; a processed food product of meat or seafood such as steamed fish paste, ham, or sausage; a dairy product such as processed milk, or fermented milk; an oil and fat or a processed food product thereof, such as salad oil, oil for deep fly, margarine, mayonnaise, shortening, whipped cream, or dressing; a seasoning such as sauce, or gravy; soup, stew, salad, delicatessen, pickle, or bread; a nutritional food for enteral administration; a functional food, or the like.

Among them, it is preferable that the food or drink be a functional food with activities for improving lipid metabolism to be used for suppression of body weight gain, reduction of body fat, and reduction of blood lipid levels.

The feed containing the agent for improving lipid metabolism according to the present invention is a feed containing αs-casein as an active ingredient thereof and having activities for improving lipid metabolism. The feed may be used for various applications utilizing activities for improving lipid metabolism. It is preferable that the feed be used for the suppression of body weight gain, the reduction of body fat, and/or the reduction of blood lipid levels.

The feed may be prepared, for example, by formulating αs-casein with a cereal such as corn, wheat, barley, rye, or milo; an oil-seed cake such as a soybean cake, a rape cake, a palm oil cake, or a linseed oil cake; a bran such as bran, wheat bran, rice bran, or defatted rice bran; lees obtained in production such as corn gluten meal or corn germ meal; an animal feed such as fish meal, powdered fat-free milk, whey, yellow-grease, or tallow; a yeast such as torula yeast, or beer yeast; a mineral feed such as calcium tertiary phosphate, or calcium carbonate; an oil and fat; an amino acid simple substance; a saccharide, or the like.

It is preferable that the feed be in a form which enables routine ingestion. Specific examples of such a form include pet food, feed for livestock, feed for fish, and the like.

The agent for improving lipid metabolism according to the present invention may be used alone, or may be used in combination with another medicinal composition, food/drink or feed, having activities for improving lipid metabolism. If the agent for improving lipid metabolism is used in combination, the activities for suppressing body weight gain, reducing body fat, reducing blood lipid levels, or the like, can be enhanced. The other medicinal composition, food/drink or feed, to be used in combination, may be formulated as an active ingredient in the medicinal composition, food/drink, or feed, according to the present invention, or may be commercialized as a separate medicine, food/drink, or the like, in combination with the medicinal composition, food/drink, or feed according to the present invention, without being formulated therein.

It is preferable that the food or drink according to the present invention be marketed as a food or drink of which the intended application purpose is indicated to be used for improving lipid metabolism, such as, for example, a "food/drink having activities for improving lipid metabolism and indicated that the food/drink is to be used for improving lipid metabolism", a "food/drink containing αs-casein and indicated as a food/drink for improving lipid metabolism", a "food/drink containing αs-casein and indicated as a food/drink for preventing body fat accumulation", or the like.

The phrases used for indicating as described above are not limited to the phrase "for improving lipid metabolism" or "for preventing body fat accumulation", for example, and other phrases may be used, provided that the phrases mean activities for improving lipid metabolism. Examples of such a phrase include phrases can make consumer recognize activities for improving lipid metabolism and/or various intended application purposes based on the activities for improving lipid metabolism.

Alternatively, the food/drink may be marketed as a food/drink of which suppression of body weight increase, reduction of body fat, and/or reduction of blood lipid level is indicated.

In the same manner, the food/drink may be marketed as a food/drink of which the intended application purpose is indicated to be used for preventing and/or improving lifestyle-related disease caused by obesity, such as hyperlipidemia, hypertension, diabetes, or the like.

The action od "indication" (indication action) includes all actions of announcing the intended application purpose to the consumer. All actions for indication fall within the "indication" action, provided that the indication evokes or suggests the intended application purpose, without depending on the purpose of indication, content of indication, object or medium to be indicated. However, it is preferable that the phrase by which the intended application purpose can be directly recognized by the consumer be indicated. In more detail, the intended application purpose may be indicated on a commercial product of the food/drink or a package thereof. In addition, transfer of the commercial product of which the intended application purpose is indicated on the commercial product or the package thereof, delivery thereof, display or import thereof for the transfer, delivery, display or distribution of a public notice, price list, or transaction document, of the commercial product, in which the intended application purpose is described, electromagnetically provision of information thereof involving the intended application purpose (via internet or the like), or the like may be considered as the indication action.

On the other hand, the content to be indicated (indicated content) is preferably one showing acceptance by the administration or the like (such as one showing that the product is accepted based on various system established by the administration and is an aspect based on such an acceptance), and such an indicated content is preferably provided on the package, container, catalogue, pamphlet, advertisement on a point of purchase (POP), other documents, or the like.

An indication of health food, functional food, nutritional food for enteral administration, food for a specified use, food with a health claim, food for a specified health use, food with a nutrient function claim, quasi drug, or the like can be exemplified. In particular, an indication of acceptance by the Ministry of Health, Labor and Welfare, such as, an indication of acceptance on the basis of the system of food for specified health uses or the similar system can be exemplified. Examples of the latter include an indication of food for a specified health use, an indication of qualified food for a specified health use, an indication of the possibility of influencing the physical structure or function, an indication of the possibility of reducing disease risk, and the like. In more detail, an indication of food for a specified health use on the basis of the Enforcement Regulation of Health Promotion Law (Ordinance No. 86 of the Ministry of Health, Labour and Welfare in Japan issued on Apr. 30, 2003) (particularly, indication of health use), and the similar indication can be mentioned as typical examples.

The activities of $\alpha$s-casein for improving lipid metabolism can be evaluated, for example, by a test using an animal model of dietary-induced obesity yielded from a typical animal free from a genetic background that causes obesity by changing the content ratios of the lipid and the carbohydrate in feed in accordance with the description on Obesity Research, Vol. 10, 2002, Pages 956 to 963. That is, the obesity and hyperlipidemia are caused by raising the animals with a high fat feed containing a high content of the lipid in accordance with conventional methods, and effects of $\alpha$s-casein on the symptoms (suppression of body weight gain, suppression of body fat increase, and suppression of blood lipid level increase) can be evaluated as the activities of $\alpha$s-casein for improving lipid metabolism.

EXAMPLES

In the following, the present invention will be circumstantially explained by indicating some examples. However, the present invention is not limited to the following examples.

Example 1

Preparation of $\alpha$s-Casein 2.4 L of a strong anionic exchanger (manufactured by Pharmacia Corporation) equilibrated with 0.02 M Tris-HCL buffer (pH 8.0) containing 4M urea and $6.5 \times 10^{-5}$ M dithiothreitol were prepared. The buffer was removed from the strong anionic exchanger, and then 90 g of sodium casein (manufactured by MORINAGA MILK INDUSTRY CO., LTD.) dissolved in 3 L of buffer were added thereto. The strong anionic exchanger was gently stirred for approximately 30 minutes, and the supernatant was separated with a glass filter. Thus, caseins ($\alpha$-, $\kappa$-, and $\beta$-caseins) were adsorbed to the strong anionic exchanger.

Next, 1.5 L of a solution prepared by formulating 0.2M sodium chloride in the buffer were added to the strong anionic exchanger, the strong anionic exchanger was gently stirred for approximately 30 minutes, and then the supernatant was separated with a glass filter. Since the supernatant contained $\kappa$- and $\beta$-caseins, this procedure was repeatedly carried out to inhibit contamination thereof into the following fraction.

Next, 1.5 L of a solution prepared by formulating 0.3M sodium chloride in the buffer were added to the strong anionic exchanger, the strong anionic exchanger was gently stirred for approximately 30 minutes, and then the supernatant was recovered with a glass filter. The supernatant contained $\alpha$s-casein. This procedure was repeatedly carried out so as to increase the recovery rate. The obtained fraction containing $\alpha$s-casein was spray-dried or freeze-dried to be powdered, and refrigerated until use. Thus, 35 g of $\alpha$s-casein (with a purity of 99%) were prepared.

Example 2

Preparation of Tableted Agent for Improving Lipid Metabolism 100 g of lactulose powders (manufactured by MORINAGA MILK INDUSTRY CO., LTD.), 635 g of maltodextrin (manufactured by Matsutani Chemical industry Co., Ltd.), 85 g of powdered fat-free milk (manufactured by MORINAGA MILK INDUSTRY CO., LTD.), 1 g of stevia sweetener (manufactured by San-Ei Gen F.F.I., Inc.), 5 g of yoghurt flavor (manufactured by San-Ei Gen F.F.I., Inc.), and 24 g of glycerin fatty acid ester formulation (manufactured by RIKEN VITAMIN CO., LTD.) were added to 150 g of $\alpha$s-casein prepared in Example 1 and then mixed uniformly. 1,800 tablets (approximately 900 g) of tableted agent for improving lipid metabolism containing $\alpha$s-casein were prepared by continuously tableting 0.5 g of the mixed powders per tablet using a tableting machine (manufactured by HATA IRON WORKS CO., LTD.) at a tableting speed of 12 tablets/ minute at a pressure of 9.8 KPa. The content of αs-casein per tablet was approximately 15% by mass.

Example 3

Preparation of Nutritional Food Powders for Enteral Administration Containing Agent for Improving Lipid Metabolism An aqueous phase was prepared in a tank by dissolving 10 kg of whey protein hydrolysate (manufactured by MORINAGA MILK INDUSTRY CO., LTD.), 36 kg of dextrin (manufactured by Showa Sangyo Co., Ltd.), and a small amount of water-soluble vitamins and minerals in 200 kg of water. Apart from the aqueous phase, 3 kg of soybean salad oil (manufactured by Taiyo-yushi Co., Ltd.), 8.5 kg of palm oil (manufactured by Taiyo-yushi Co., Ltd.), 2.5 kg of safflower oil (manufactured by Taiyo-yushi Co., Ltd.), 0.2 kg of lecithin (manufactured by AJINOMOTO CO., INC.), 0.2 kg of fatty acid monoglyceride (manufactured by KAO CORPORATION), and a small amount of fat-soluble vitamins were mixed and dissolved to prepare an oil phase. The oil phase was added to the aqueous phase in the tank, and stirred to mix them. Then, the mixture was heated at 70° C., and then homogenized at a pressure of 14.7 MPa using a homogenizer. Then, the resultant was sterilized at 90° C. for ten minutes, and then concentrated and spray-dried to prepare approximately 59 kg of intermediate powders. 6.8 kg of cane sugar (manufactured by HOKUREN), 167 g of mix-powders of amino acids (manufactured by AJINOMOTO CO., INC.), and 1 kg of αs-casein prepared in Example 1 were added to 50 kg of the intermediate powders, and uniformly mixed to prepare approximately 56 kg of nutritional food powders for enteral administration containing αs-casein.

Example 4

Preparation of Stew Containing αs-Casein and Having Activities for Improving Lipid Metabolism One-half of an onion cut into 1 cm squares was fried in 7 g of butter, and then two-third tablespoons of soft flour was added thereto and further fried. 200 ml of water and one-third teaspoons of granule bouillon were added to the resultant and stirred to dissolve the resultant. One potato cut into 1 cm squares, 15 g of roast ham, and one-third cans of mix beans were added to the resultant and boiled. When the potato softened, 15 g of αs-casein prepared in the same way as that of Example 1 were added and boiled again, followed by adding salt and pepper to taste. Thus, the stew containing αs-casein and having activities for improving lipid metabolism was prepared.

Example 5

Preparation of Orange Milk Jelly Containing αs-Casein and Having Activities for Improving Lipid Metabolism An orange was peeled and the obtained orange peel was finely minced. 5 g of gelatine powders (manufactured by JELLICE Co., Ltd.) were added to 50 ml of water to turn the gelatin powders into a liquid state. 40 g of αs-casein prepared in the same way as that of Example 1, three tablespoons of granulated sugar, and 100 ml of water were put in a pan and the mixture was heated. Heating of the mixture was stopped immediately before boiling, and the gelatine soaked in water was added thereto and dissolved by the residual heat. After the gelatine was dissolved, and the resultant was cooled with ice-water till thickened, 150 ml of orange juice, the minced orange peel, and one tablespoon of COINTREAU were added to the resultant, and kept cool in the refrigerator for 2-3 hours to prepare an orange milk jelly containing αs-casein and having activities for improving lipid metabolism.

In the following, some test examples will be shown.

Test Example 1

Test-1 for Checking Activities

Activities of αs-casein for suppressing body weight gain was checked by administering various casein solutions while high fat feed was ingested and checking the variation in the body weight. For the purpose of comparison, sodium casein, which is a casein mixture containing (αs-casein, β-casein, and κ-casein, was also administered. In addition, a feed containing a normal amount of fat (of which the calories have been adjusted with carbohydrates) (normal fat feed) was prepared, and the lower limit of the body weight when the normal fat feed was ingested was checked.

(1) Feed

The high fat feed composed of components shown in Table 1 (hereinafter, abbreviated as HF) was prepared. The normal fat feed composed of components shown in Table 2 (hereinafter, abbreviated as NF) was prepared.

TABLE 1

|  | g | kcal |
|---|---|---|
| Protein | 23.4 | 20 |
| Carbohydrate | 41.6 | 35 |
| Fat | 23.7 | 45 |
| Total |  | 100 |
| kcal/g | 4.73 |  |
| Items |  |  |
| Soybean protein | 200 | 800 |
| Corn starch | 72.8 | 291 |
| Maltodextrin | 100 | 400 |
| Sucrose | 172.8 | 691 |
| Cellulose | 50 | 0 |
| Soybean oil | 25 | 225 |
| Lard | 177.5 | 1598 |
| Mineral mix S10026 | 10 | 0 |
| Calcium diphosphate | 13 | 0 |
| Calcium carbonate | 5.5 | 0 |
| Potassium citrate monohydrate | 16.5 | 0 |
| Vitamin mix | 10 | 40 |
| Choline tartarate | 2 | 0 |
| Total | 855.2 | 4045 |

TABLE 2

|  | g | kcal |
|---|---|---|
| Protein | 19 | 20 |
| Carbohydrate | 67.5 | 70 |
| Fat | 4.3 | 10 |
| Total |  | 100 |
| kcal/g | 3.84 |  |
| Items |  |  |
| Soybean protein | 200 | 800 |
| Corn starch | 315 | 1260 |
| Maltodextrin | 35 | 140 |

TABLE 2-continued

|  | g | kcal |
|---|---|---|
| Sucrose | 350 | 1400 |
| Cellulose | 50 | 0 |
| Soybean oil | 25 | 225 |
| Lard | 20 | 180 |
| Mineral mix S10026 | 10 | 0 |
| Calcium diphosphate | 13 | 0 |
| Calcium carbonate | 5.5 | 0 |
| Potassium citrate monohydrate | 16.5 | 0 |
| Vitamin mix | 10 | 40 |
| Choline tartarate | 2 | 0 |
| Total | 1052.05 | 4045 |

(2) Preparation of Samples

Control Sample: Distilled Water for Injection $\alpha s$-Cs sample: 200 mg of $\alpha s$-casein (manufactured by SIGMA) were dissolved in 40 ml of distilled water for injection (manufactured by OTSUKA PHARMACEUTICAL CO., LTD.) to prepare the sample (protein content: 5 mg/ml).

$\beta$-Cs sample: 200 mg of $\beta$-casein (manufactured by SIGMA) were dissolved in 40 ml of distilled water for injection (manufactured by OTSUKA PHARMACEUTICAL CO., LTD.) to prepare the sample (protein content: 5 mg/ml).

$\kappa$-Cs sample: 200 mg of $\kappa$-casein (manufactured by SIGMA) was dissolved in 40 ml of distilled water for injection (manufactured by OTSUKA PHARMACEUTICAL CO., LTD.) to prepare the sample (protein content: 5 mg/ml).

Cs—Na sample: 200 mg of purified sodium casein (manufactured by Wako Pure Chemical Industries, Ltd.) was dissolved in 40 ml of distilled water for injection (manufactured by OTSUKA PHARMACEUTICAL CO., LTD.) to prepare the sample (protein content: 5 mg/ml).

(3) Test Animal

Four-week-old ICR male mice, purchased from Japan SLC, Inc., were used.

(4) Test Method

First, the mice were fed for one week with the high fat feed, and then divided into six groups each consisting of eight mice having equivalent body weights. The mice were allowed to ingest feed and water freely. In addition, each sample was administered orally at a dose of 0.5 ml/mouse once a day for five days per week via a gastric tube. Each sample administered to each group was described below.

Group 1 (negative control: hereinafter, abbreviated as NC group): Feed NF and the control sample.

Group 2 (positive control: hereinafter, abbreviated as PC group): Feed HF and the control sample.

Group 3 ($\alpha s$-casein-administered group: hereinafter, abbreviated as $\alpha s$ group): Feed HF and $\alpha s$-Cs sample.

Group 4 ($\beta$-casein-administered group: hereinafter, abbreviated as $\beta$ group): Feed HF and $\beta$-Cs sample.

Group 5 ($\kappa$-casein-administered group: hereinafter, abbreviated as $\kappa$ group): Feed HF and $\kappa$-Cs sample.

Group 6 (sodium casein-administered group: hereinafter, abbreviated as Cs—Na group): Feed HF and Cs—Na sample (5) Test Results Although each amount of the ingested feed was checked once a week in the test term, no difference was recognized among the groups. Each average body weight for each group at eight weeks after the beginning of the administration are shown in Table 3. Although the body weight in each group varied a great deal and a significant difference among the groups was not recognized, the body weight increase of the "$\alpha s$ group to which the $\alpha s$-Cs sample was administered with high fat feed" was definitely suppressed in comparison with that of the "PC group to which the control sample was administered with high fat feed".

In addition, the body weight of the $\alpha s$ group at the point of eight weeks in the administration was approximately the same as that of the "NC group to which the control sample was administered with the normal fat feed", and excess reduction of the body weight of the $\alpha s$ group at the point of eight weeks in the administration period was not recognized. Thus, it was demonstrated that the metabolism of the excess lipid accumulated in the living body was accelerated in the $\alpha s$ group and there was almost no influence to decrease essential lipids.

TABLE 3

| Group | Sample | Average body weight (g) |
|---|---|---|
| 1 | NC | 46.9 |
| 2 | PC | 51.6 |
| 3 | $\alpha s$ | 45.7 |
| 4 | $\beta$ | 50.0 |
| 5 | $\kappa$ | 48.9 |
| 6 | Cs—Na | 55.0 |

Test Example 2

Test-2 for Checking Activities

The activities of $\alpha s$-casein for suppressing an increase of body fat such as visceral fat and subcutaneous fat were checked by measuring the weight of the visceral (intraperitoneal) fat, the weight of the subcutaneous fat, the lean body mass, and the body fat ratio, using a CT scanner for small animals, when various casein solution was administered while allowing ingestion of high fat feed, to monitor the variation thereof. In addition, a feed containing a normal amount of fat (normal fat feed) was prepared, and the lower limit of the above-mentioned weights and the body fat ratio when the normal fat feed was ingested.

(1) Feed

The same kinds of feed as those of Test Example 1 were used.

(2) Preparation of Samples

The same kinds of samples as those of Test Example 1 were used.

(3) Test Animal

The same kind of test animals as those of Test Example 1 were used.

(4) Test Method

First, mice were fed for one week with the high fat feed, and then divided into six groups each consisting of eight mice having equivalent body weights. The mice were allowed to ingest feed and water freely. In addition, each sample was administered orally at a dose of 0.5 ml/mouse once a day for five days per week via a gastric tube. The feed and sample administered to each group were the same as those of Test Example 1.

The weight of the abdomenvisceral (intraperitoneal) fat, the weight of the subcutaneous fat, and the body fat ratio, of two or three mice of which each body weight is approximately equal to the average body weight in each group were measured using a CT scanner for small animals (manufactured by ALOKA CO., LTD.: LaTheta (trademark)) at the points of two weeks, four weeks and six weeks in the administration period.

In addition, the weight of the abdomen subcutaneous fat, the weight of the visceral fat, the lean body mass, and the body fat ratio of each mouse was measured using the CT scanner for small animals at the point of eight weeks in the administration period.

(5) Test Results

Although each amount of the ingested feed was checked once a week in the test term, no difference was recognized among the groups. Each average of the weight of the abdomen subcutaneous fat, the weight of the visceral (intraperitoneal) fat, and the lean body mass of each group at the point of eight weeks in the administration period are shown in Tables 4 to 6. The average body fat ratio at the point of eight weeks in the administration period is shown in Table 7.

It was revealed that the "PC group to which the control sample was administered with the high fat feed" exhibited a significant increase in the weight of the adipose tissues but exhibited a decrease in the lean body mass, in comparison with the "NC group to which a control sample was administered with the normal fat feed". There were significant differences in both the weight of visceral fat and the weight of subcutaneous fat between the NC group and the PC group, and therefore it was revealed that the body weight gain recognized in the PC group of Test Example 1 resulted from the fat weight increase in the body.

It was revealed that the body fat ratio reflected the results and the body fat ratio of the PC group was significantly greater than that of the NC group as shown in Table 7.

On the other hand, the "αs group to which the αs-Cs sample was administered with the high fat feed" was significantly prevented from increasing in both the weight of the visceral fat and the weight of the subcutaneous fat in spite of ingestion of the high fat feed, in comparison with the PC group. In addition, body fat ratio was also significantly decreased.

However, the suppression degree of body fat accumulation in the αs group was approximately equal to that in the NC group, and the adipose tissues were neither excessively decreased nor lost by ingesting the αs-Cs sample. On the other hand, the decrease of the lean body mass in the αs group was not significant in comparison with that in the PC group, and it was considered that the suppression of a body weight increase exhibited by administering the αs-Cs sample was almost due to the suppression of the weight increase of the adipose tissues. In addition, effects of maintaining the weight of tissues excluding the adipose tissues (the lean body mass) at a normal level was recognized.

The β group, the κ group, and the Cs—Na group, to which casein other than αs-Cs was administered, exhibited almost the same levels of visceral fat weight and subcutaneous fat weight as those of the PC group at the point of eight weeks in the administration period, and no suppressive effects against the weight increase of the adipose tissues was recognized.

TABLE 4

| Group | Sample | Average weight of subcutaneous fat (g) |
|---|---|---|
| 1 | NC | 1.114* |
| 2 | PC | 3.165 |
| 3 | αs | 1.158* |
| 4 | β | 2.420 |
| 5 | κ | 2.142 |
| 6 | Cs—Na | 3.069 |

There is a significant difference (*P < 0.05) in comparison with PC.

TABLE 5

| Group | Sample | Average weight of intraperitoneal fat (g) |
|---|---|---|
| 1 | NC | 2.103* |
| 2 | PC | 5.240 |
| 3 | αs | 2.818* |
| 4 | β | 5.737 |
| 5 | κ | 5.205 |
| 6 | Cs—Na | 6.044 |

There is a significant difference (*P < 0.05) in comparison with PC.

TABLE 6

| Group | Sample | Average weight of the abdomen lean body mass (g) |
|---|---|---|
| 1 | NC | 20.168 |
| 2 | PC | 18.491 |
| 3 | αs | 19.156 |
| 4 | β | 17.887 |
| 5 | κ | 17.854 |
| 6 | Cs—Na | 19.505 |

TABLE 7

| Group | Sample | Average body fat ratio (%) |
|---|---|---|
| 1 | NC | 13.6* |
| 2 | PC | 27.8 |
| 3 | αs | 16.5* |
| 4 | β | 30.9 |
| 5 | κ | 28.5 |
| 6 | Cs—Na | 30.8 |

There is a significant difference (*P < 0.05) in comparison with PC.

FIG. 1 is a graph showing variation of visceral fat weight over the administration period. The degree of the weight increase seen in the PC group was not seen in the NC group at two weeks or later after the beginning of the administration (NC group: 1.6 g, PC group: 2.1 g). The αs group exhibited a weight increase in a similar manner to that of the PC group and other casein groups until two weeks after the beginning of the administration (the αs group: 2.5 g, the β group: 2.1 g, the κ group: 2.7 g, the Cs—Na group: 2.5 g). At the end of the administration, a weight decrease was recognized in the αs group, and the weight of the αs group at six weeks after the administration was below that of the NC group (NC group: 1.7 g, the αs group: 0.9 g). The weight of the αs group recovered to approximately the same level of the weight of the NC group (NC group: 2.1 g, the αs group: 2.9 g).

Figure 2:
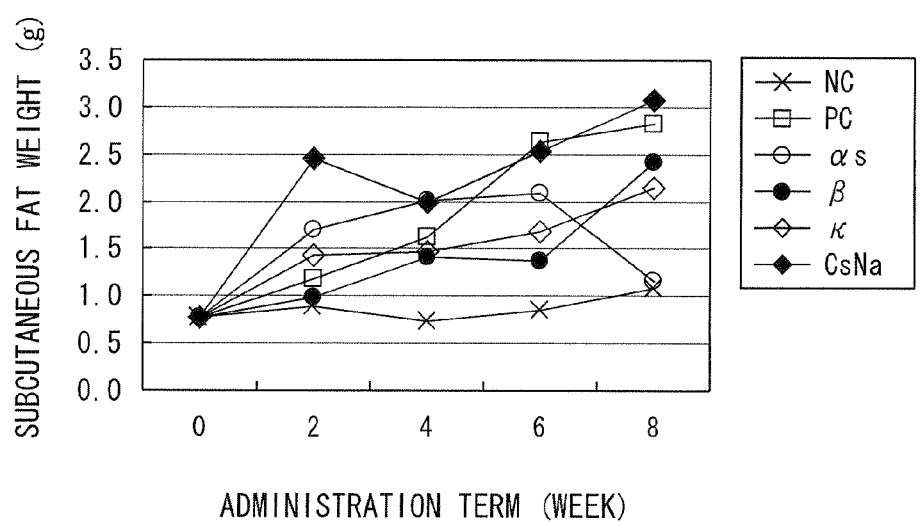
FIG. 2 is a graph showing the variation of subcutaneous fat weight in a test over the administration period.

FIG. 2 is a graph showing variation of subcutaneous fat weight over the administration period. Although the weight of the subcutaneous fat was significantly increased in the αs group at two to four weeks after the beginning of the administration in a similar manner to that of the PC group (PC group: 1.6 g, the αs group: 2.0 g), the rate of the weight increase became moderate after that, and drastically lowered at the point of eight weeks in the administration period (PC group: 2.8 g, the αs group: 1.2 g).

Figure 3:
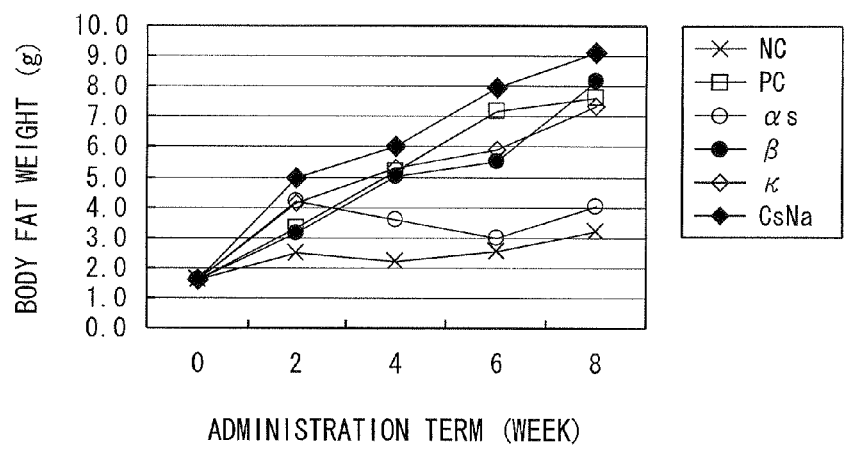
FIG. 3 is a graph showing the variation of the total body fat mass of visceral fat and subcutaneous fat in a test over the administration period.

FIG. 3 is a graph showing variation of the total body fat weight of visceral fat weight and subcutaneous fat weight over the administration period. Although the body fat weight increase in the αs group was seen until two weeks after the beginning of the administration in a similar manner to that of the PC group and other casein groups (PC group: 3.3 g, the αs group: 4.2 g, the β group: 3.1 g, the κ group: 4.1 g, the Cs—Na group: 4.9 g), the increase curve thereof became moderate after that, and then the weight decreased. After the weight was decreased to the same level as that of the NC group at the point of six weeks in the administration period (at six weeks, NC group: 2.6 g, the αs group: 3.0 g), the weight was increased again in a similar manner to that of the NC group again (at eight weeks, NC group: 3.2 g, the αs group: 4.1 g).

Figure 4:
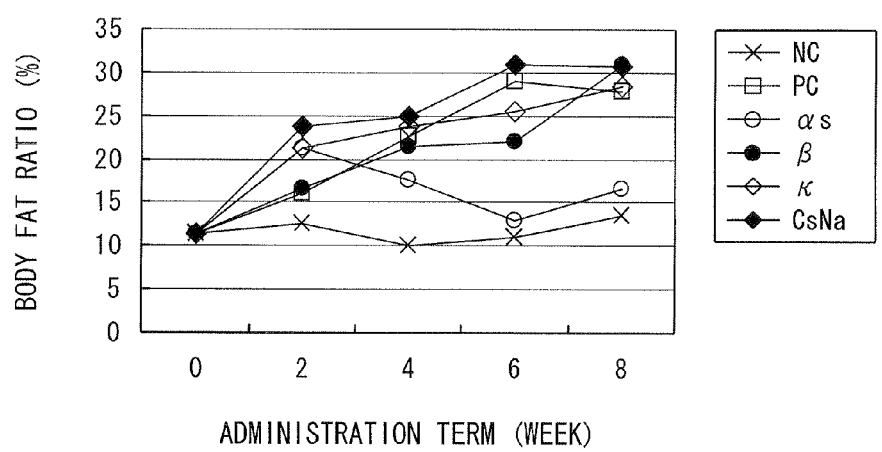
FIG. 4 is a graph showing the variation of the body fat ratio in a test over the administration period.

It was considered that the moderate increase in body fat weight in the NC group and the αs group after six weeks as shown in FIG. 3 was a natural phenomenon due to aging. It was revealed that the body fat ratio was not drastically increased as shown in the graph of FIG. 4 showing variation of the body fat ratio over the administration period. However, it was revealed that the body fat ratio in the PC group, the β group, the κ group, and the Cs—Na group was significantly increased during the two-week to eight-week in the administration period.

Test Example 3

Test-3 for Checking Activities

The activities for suppressing fat accumulation in the body, recognized in Test Example 2, were checked. The animals were dissected after eight weeks of the administration to measure regional weight of visceral (intraperitoneal) fat.
(1) Feed
The same kinds of feed as those of Test Example 1 were used.
(2) Preparation of Samples
The same kinds of samples as those of Test Example 1 were used.
(3) Test Animal
The same kind of test animals as those of Test Example 1 were used.
(4) Test Method
First, the test animals were fed for one week with the high fat feed, and then divided into six groups each consisting of eight mice having equivalent body weights. The mice were allowed to ingest feed and water freely. In addition, each sample was administered orally at a dose of 0.5 ml/mouse once a day for five days per week via a gastric tube. The kinds of the feed and samples administered to each group were the same as those of Test Example 1.

All the mice were dissected at eight weeks after the beginning of the administration and the visceral fat was removed from the epididymal, the mesentery, and the retroperitoneum, and the fat weight of each portion was measured.
(5) Test Results
The test results are shown in Table 8. It was revealed that the NC group had significantly less visceral fat weight in all of the three portions than that of the PC group, by comparing the NC group with the PC group in terms of each weight of the visceral fat obtained from each of the three portions.

The αs group had significantly less weight of the visceral fat in two portions of the surrounding epididymal and the mesentery, and particularly had approximately the same weight of the visceral fat in the mesentery as that of the NC group. Although no significant difference was seen, it was seen that the weight of the visceral fat in the retroperitoneum was distinctly small. In contrast, no difference was recognized between the PC group and each group to which another kind of casein was administered (the β group, the κ group, or the Cs—Na group).

Although the amount of ingested feed was checked once a week in the test term, no difference was recognized among the groups.

TABLE 8

| Group | Sample | Average fat weight of the epididymal (g) | Average fat weight of the mesentery (g) | Average fat weight of the retroperitoneum (g) |
|---|---|---|---|---|
| 1 | NC | 1.131* | 0.495* | 0.337* |
| 2 | PC | 3.075 | 0.968 | 0.714 |
| 3 | αs | 1.614** | 0.529** | 0.450 |
| 4 | β | 3.280 | 0.963 | 0.796 |
| 5 | κ | 2.861 | 0.871 | 0.758 |
| 6 | Cs—Na | 3.253 | 1.078 | 0.811 |

There is a significant difference (*P < 0.01) in comparison with PC.
There is a significant difference (**P < 0.05) in comparison with PC.

Test Example 4

Test-4 for Checking Activities

The blood lipid levels were measured after each casein solution was administered while allowing to ingest high fat feed, in order to check the activities of αs-casein for reducing the blood lipid levels. In addition, a feed containing the normal amount of fat (normal fat feed) was prepared to check the blood lipid levels when the normal fat feed was ingested.
(1) Feed
The same kinds of feed as those of Test Example 1 were used.
(2) Preparation of Samples
The same kinds of samples as those of Test Example 1 were used.
(3) Test Animal
The same kind of test animals as those of Test Example 1 were used.
(4) Test Method
First, the test animals were fed for one week with the high fat feed and then divided into six groups each consisting of eight mice having equivalent body weights. The mice were allowed to ingest feed and water freely. In addition, each sample was administered orally at a dose of 0.5 ml/mouse once a day for five days per week via a gastric tube. The kinds of the feed and samples administered to each group were the same as those of Test Example 1.

All the mice of each group were dissected at eight weeks after the beginning of the administration and blood samples for each mouse were collected. The serum lipids were analyzed using an automatic clinical chemistry analyzer (manufactured by ARKRAY, Inc.: SPOTCHEM (trademark)) to measure the total cholesterol (T-Cho, unit: mg/dL) and the neutral lipids (TG, unit: mg/dL).
(5) Test Results
The test results are shown in Table 9. Although there was a significant difference in T-Cho level between the NC group and the PC group, there were no differences among the other groups. It was recognized that the αs group exhibited low levels of both T-Cho and TG, and administration of αs-casein achieved suppression of blood lipid levels. Although each amount of the ingested feed was checked once a week in the test term, no difference was recognized among the groups.

TABLE 9

| Group | Sample | T-Cho | TG |
|---|---|---|---|
| 1 | NC | 118.0* | 127.0 |
| 2 | PC | 179.6 | 97.8 |
| 3 | αs | 150.4 | 85.1 |

TABLE 9-continued

| Group | Sample | T-Cho | TG |
|---|---|---|---|
| 4 | β | 169.3 | 122.7 |
| 5 | κ | 166.7 | 220.3 |
| 6 | Cs—Na | 175.0 | 165.3 |

There is a significant difference (*P < 0.05) in comparison with PC.

Test Example 5

Test-1 for Checking Dose Dependency

Figure 5:
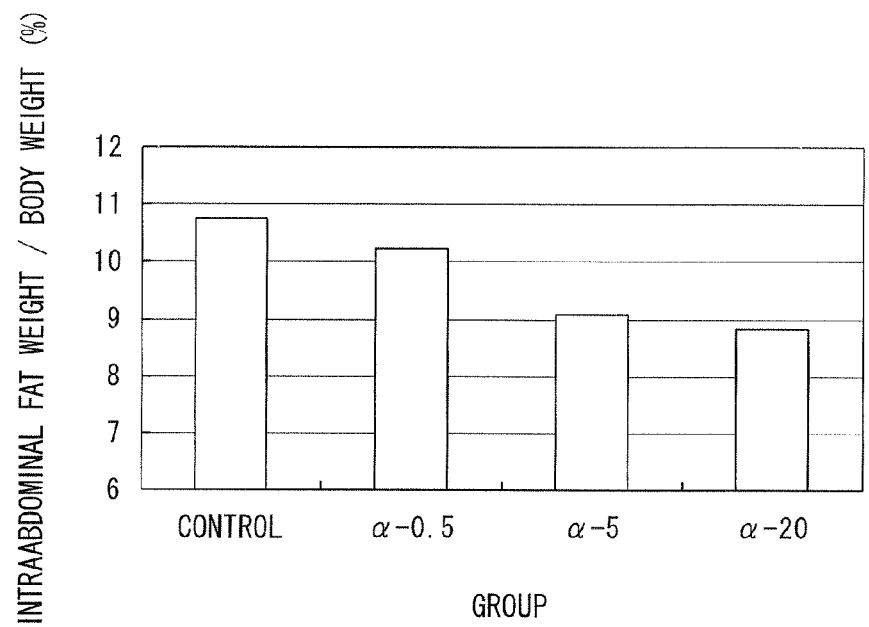
FIG. 5 is a graph showing the relationship between the dose of αs-casein and the ratio of intraperitoneal fat weight with respect to the body weight in a test over the administration period.

Various αs-casein solutions with different concentrations thereof were administered to test animals fed high fat feed and the visceral fat weight per body weight thereof was measured to check an effective dose of αs-casein for improving lipid metabolism in the body.
(1) Feed
The same kinds of feed as those of Test Example 1 were used.
(2) Preparation of Samples
Control Sample: Distilled Water for Injection
αs-Cs sample: αs-casein (manufactured by SIGMA) was dissolved in the distilled water for injection (manufactured by OTSUKA PHARMACEUTICAL CO., LTD.) to obtain a protein concentration of 0.5 mg/ml, 5 mg/ml, or 20 mg/ml.
(3) Test Animals
The same kind of test animals as those of Test Example 1 were used.
(4) Test Method
First, the test animals were fed for one week with the high fat feed, and then divided into six groups each consisting of eight mice having equivalent body weights. The mice were allowed to ingest feed and water freely. In addition, each sample was administered orally at a dose of 0.5 ml/mouse once a day for five days per week via a gastric tube. All the mice of each group were measured the body weight thereof and then dissected after the test term was ended, and the weight of the intraperitoneal fat thereof was measured. The test term was twelve weeks after the mice were divided into the groups. Each group was as follows.
Group 1: the control sample was administered (Control group).
Group 2: 0.5 mg/ml of αs-casein was administered (α-0.5 group)
Group 3: 5 mg/ml of αs-casein was administered (α-5 group)
Group 4: 20 mg/ml of αs-casein was administered (α-20 group)
(5) Test Results
The test results are shown in FIG. 5. As the results, the ratio of the intraperitoneal fat weight with respect to the body weight of the control group at twelve weeks after the beginning of the administration was 10.8%, while the ratio of the intraperitoneal fat weight with respect to the body weight was decreased in a dose-dependent manner of αs-casein, and that of the α-0.5 group was 10.2%, that of the α-5 group was 9.1%, and that of the α-20 group was 8.8%. Although the amount of the ingested feed was checked once a week in the test term, no difference was recognized among the groups.
As a result, it was recognized that favorable results were exhibited, that is, the ratio of the intraperitoneal fat weight with respect to the body weight was distinctly decreased by administering αs-casein solution with a protein concentration of 5 mg/ml or more. The dosage of αs-casein solution with a protein concentration of 5 mg/ml was equivalent to 80 mg/kg body weight per day.

Test Example 6

Test-2 for Checking Dose Dependency

Figure 6:
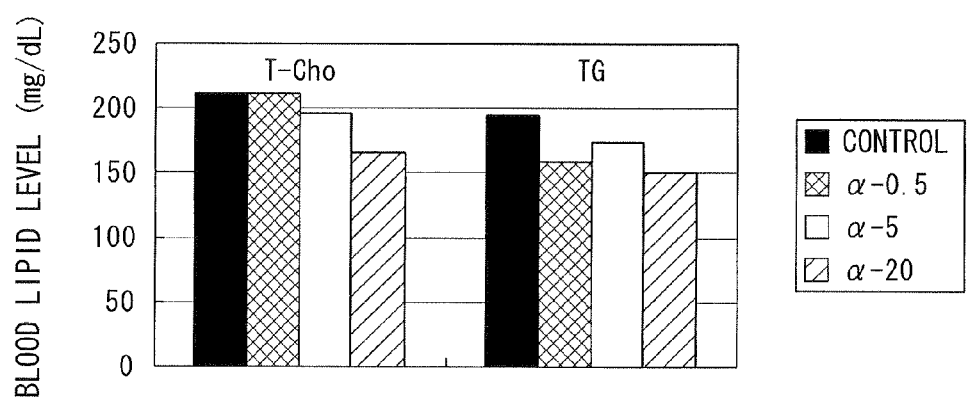
FIG. 6 is a graph showing the relationship between the dose of αs-casein and blood lipid levels in a test.

Various αs-casein solutions with different concentrations were administered to test animals fed high fat feed and the blood lipid levels thereof were measured.
(1) Feed
The same kinds of feed as those of Test Example 1 were used.
(2) Preparation of Samples
The same kinds of samples as those of Test Example 5 were used.
(3) Test Animal
The same kind of test animals as those of Test Example 1 were used.
(4) Test Method
First, the test animals were fed for one week with the high fat feed, and then divided into six groups each consisting of eight mice having equivalent body weights. The mice were allowed to ingest feed and water freely. In addition, each sample was administered orally at a dose of 0.5 ml/mouse once a day for five days per week via a gastric tube. All the mice of each group were dissected after the test term (twelve weeks) was ended, and blood was collected by cardiac puncture. The collected blood was put into a tube for serum separation (manufactured by COSMO BIO co., ltd.) filled with a coagulation-accelerator-type separating agent in advance and the serum thereof was separated. The contents of T-Cho and TG in the serum were measured using an automatic clinical chemistry analyzer (manufactured by ARKRAY, Inc.: SPOTCHEM (trademark)). The free fatty acid level in the serum was measured using an NEFA-C Test Wako (manufactured by Wako Pure Chemical Industries, Ltd.). Each group was as follows.
Group 1: the control sample was administered (Control group).
Group 2: 0.5 mg/ml of αs-casein was administered (α-0.5 group)
Group 3: 5 mg/ml of αs-casein was administered (α-5 group)
Group 4: 20 mg/ml of αs-casein was administered (α-20 group)
(5) Test Results
The measurement results of the T-Cho and TG contents are shown in FIG. 6. The results revealed that the control group resulted in the T-Cho content of 211.8 mg/dL and the TG content of 195.1 mg/dL, while both the T-Cho and TG contents were decreased in a dose-dependent manner in the groups to which αs-casein was administered, the α-0.5 group resulted in the T-Cho content of 211.6 mg/dL and the TG content of 158.9 mg/dL, the α-5 group resulted in the T-Cho content of 196.3 mg/dL and the TG content of 174.4 mg/dL, and the α-20 group resulted in the T-Cho content of 166.1 mg/dL and the TG content of 149.9 mg/dL.
It was seen that favorable results were exhibited, that is, both the T-Cho and TG contents were distinctly decreased in comparison with those of the control group, by administering αs-casein solutions with a protein concentration of 5 mg/ml or more. Although each amount of the ingested feed was checked once a week in the test term, no difference was recognized among the groups.

Figure 7:
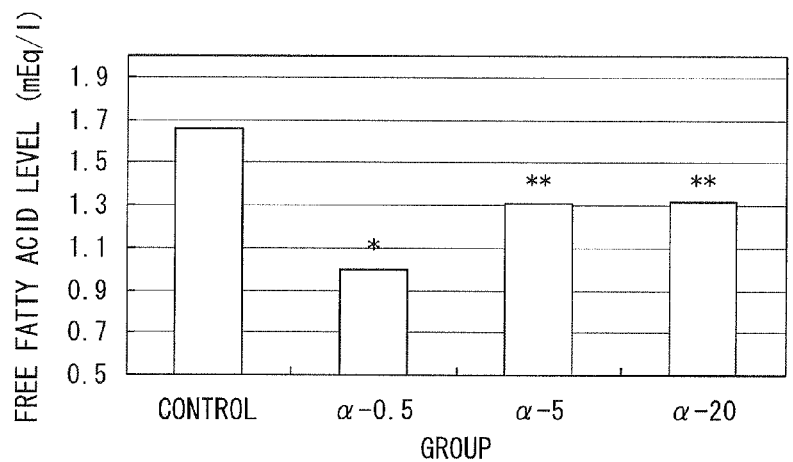
FIG. 7 is a graph showing the relationship between the dose of αs-casein and the free fatty acid levels of blood in a test.

In addition, the measurement results of the free fatty acid level in blood are shown in FIG. 7. The results revealed that the free fatty acid level in blood of the control group was 1.661 mEq/l, while that of the α-0.5 group was 0.999 mEq/l, that of the α-5 group was 1.305 mEq/l, and that of the α-20 group was 1.312 mEq/l. Thus, it was recognized that all the groups to which αs-casein was administered resulted in significant decrease in the free fatty acid level of the blood in comparison with that of the control group.

INDUSTRIAL APPLICABILITY

According to the present invention, an agent for improving lipid metabolism which is highly safe for human and animals and can reduce (induce and keep remission of) lifestyle-related diseases symptoms caused by obesity, such as, for example, hyperlipidemia, hypertension, or diabetes, by routine administration or ingestion thereof, can be provided. In addition, αs-casein, which is an active ingredient according to the present invention, can be prepared on a large scale from a raw material such as milk, and therefore the agent for improving lipid metabolism, or the food/drink or feed containing the agent can be provided at a low cost.

The invention claimed is:

1. A method for treating obesity, comprising:
   administering an effective amount of medicinal composition consisting of αs-casein and at least one pharmaceutically acceptable additive to a mammal in need thereof.

2. The method of claim 1, wherein the effective amount of the αs-casein is from 80 mg/kg body weight per day to 320 mg/kg body weight per day.

3. The method of claim 1, wherein the pharmaceutically acceptable additive is selected from the group consisting of a vehicle, binder, disintegrant, lubricant, stabilizer, taste- and smell-masking agent, diluent, and solvent for injection.

4. The method of claim 1, wherein an amount of the αs-casein in the medicinal composition is 0.1 to 90% by mass relative to the mass of the medicinal composition.

5. The method of claim 1, wherein an amount of the αs-casein in the medicinal composition is 0.5 to 40% by mass relative to the mass of the medicinal composition.

6. The method of claim 1, wherein an amount of the αs-casein in the medicinal composition is 1 to 20% by mass relative to the mass of the medicinal composition.

7. A method for treating obesity, comprising:
   administering an effective amount of αs-casein alone to a mammal in need thereof.

8. The method of claim 7, wherein the effective amount of the αs-casein is from 80 mg/kg body weight per day to 320 mg/kg body weight per day.

9. A method for treating hyperlipidemia, comprising:
   administering an effective amount of medicinal composition consisting of αs-casein and at least one pharmaceutically acceptable additive to a mammal in need thereof.

10. The method of claim 9, wherein the effective amount of the αs-casein is from 80 mg/kg body weight per day to 320 mg/kg body weight per day.

11. The method of claim 9, wherein the pharmaceutically acceptable additive is selected from the group consisting of a vehicle, binder, disintegrant, lubricant, stabilizer, taste- and smell-masking agent, diluent, and solvent for injection.

12. The method of claim 9, wherein an amount of the αs-casein in the medicinal composition is 0.1 to 90% by mass relative to the mass of the medicinal composition.

13. The method of claim 9, wherein an amount of the αs-casein in the medicinal composition is 0.5 to 40% by mass relative to the mass of the medicinal composition.

14. The method of claim 9, wherein an amount of the αs-casein in the medicinal composition is 1 to 20% by mass relative to the mass of the medicinal composition.

15. A method for treating hyperlipidemia, comprising:
    administering an effective amount of αs-casein alone to a mammal in need thereof.

16. The method of claim 15, wherein the effective amount of the αs-casein is from 80 mg/kg body weight per day to 320 mg/kg body weight per day.

* * * * *